(12) United States Patent
Puig Torres et al.

(10) Patent No.: US 7,807,827 B2
(45) Date of Patent: Oct. 5, 2010

(54) PROCEDURE FOR PREPARING 11-(4-[2-(2-HYDROXYETHOXY)ETHYL]-1-PIPERAZINEYL)-DIBENZO[B,F] [1,4]THIAZEPINE

(75) Inventors: Salvador Puig Torres, Barcelona (ES); Reyes Herbera Espinal, Barcelona (ES); Pere Dalmases Barjoan, Sant Feliu de Llobregat (ES)

(73) Assignee: Inke, S.A., Castellbisbal (ES)

( * ) Notice: Subject to any disclaimer, the term of this patent is extended or adjusted under 35 U.S.C. 154(b) by 1254 days.

(21) Appl. No.: 10/566,413

(22) PCT Filed: Jul. 27, 2004

(86) PCT No.: PCT/IB2004/002527

§ 371 (c)(1), (2), (4) Date: Jan. 30, 2006

(87) PCT Pub. No.: WO2005/014590

PCT Pub. Date: Feb. 17, 2005

(65) Prior Publication Data

US 2006/0189594 A1 Aug. 24, 2006

(30) Foreign Application Priority Data

Aug. 8, 2003 (ES) .................. 200301922

(51) Int. Cl.
 *C07D 281/16* (2006.01)
(52) U.S. Cl. .................................. 540/551
(58) Field of Classification Search ............ 540/551
See application file for complete search history.

(56) References Cited

U.S. PATENT DOCUMENTS

2005/0080072 A1* 4/2005 Deshpande et al. .... 514/211.13

FOREIGN PATENT DOCUMENTS

| CH | 422793 | 4/1967 |
|---|---|---|
| EP | 0240228 | 10/1987 |
| EP | 0282236 | 9/1988 |
| WO | 9906381 | 2/1999 |
| WO | 0155125 | 8/2001 |

OTHER PUBLICATIONS

Warawa E J et al.: "Behavioral approach to nondyskinetic dopamine antagonists: Identification of Seroquel" Journal of Medicinal Chemistry, American Chemical Society. Washington, US, vol. 44, Feb. 1, 2001, pp. 372-389, XP002213291 ISSN: 0022-2623.

Lambert, T.N. et al.: "Synthesis of 3-Hydroxy-2-pyridinone Derivatives of 4-tert-Butylcalix'4lareness: A New Class of Selective Extractants of Actinide(IV) Ions" Journal of Organic Chemistry, vol. 64, 1999, pp. 6097-6101, XP002317244.

Greene. Protective Groups in Organic Synthesis, $3^{rd}$ edition, Wiley Intemscience, chapter 2, pp. 17-23; 48-51; 54-55; 76-87; 102-105; 110-111; 702-703; 706-708, 2002.

Smith et al. March's Advanced Organic Chemistry, $5^{th}$ edition, New York (USA): John Wiley & Sons; 2001, p. 446.

* cited by examiner

*Primary Examiner*—Brenda L Coleman
(74) *Attorney, Agent, or Firm*—Cozen O'Connor

(57) ABSTRACT

The invention relates to a procedure for preparing quetiapine by reaction between a compound of formula (II) and a compound of formula (III), in which X means a leaving group and P a protective group of alcohols resistant to alkaline conditions, in the presence of a base, followed by a step of deprotection and, optionally, obtaining a pharmaceutically acceptable salt thereof.

Said procedure permits the obtaining of quetiapine with a high degree of purity under soft temperature conditions, with short reaction times and avoiding the use of toxic solvents.

(Graphic)

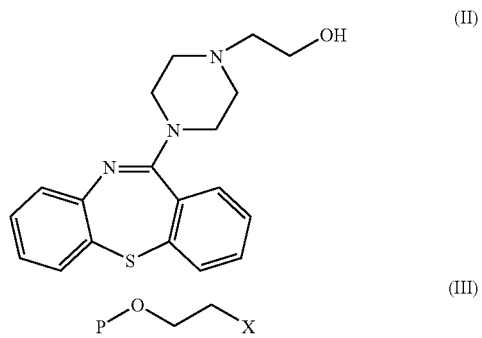

17 Claims, No Drawings

PROCEDURE FOR PREPARING 11-(4-[2-(2-HYDROXYETHOXY)ETHYL]-1-PIPERAZINEYL)-DIBENZO[B,F][1,4]THIAZEPINE

This application is a national stage of PCT International Application No. PCT/IB2004/02527, filed Jul. 27, 2004 which claims priority of Spanish Application No. 2003/01922, filed Aug. 8, 2003, the contents of all of which is hereby incorporated by reference into this application.

FIELD OF THE INVENTION

This invention relates to a new procedure for the preparation of a pharmaceutically active compound.

BACKGROUND OF THE INVENTION

Patent EP 240228 describes a dibenzothiazepine compound of formula (I):

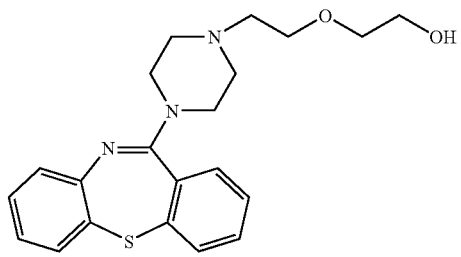

useful for its antidopaminergic activity, for example as an antipsychotic or neuroleptic, currently known by the DCI of quetiapine.

The said patent describes the obtaining of the compound of formula (I) by reaction of an imino chloride, specifically 11-chloro-dibenzo[b,f][1,4]thiazepine, or of its corresponding imino ether, with 2-(2-piperazine-1-il-ethoxy)ethanol.

A later patent, EP 282236, describes the preparation of the compound of formula (I) by reaction of the same imino chloride with piperazine, followed by reaction of the product obtained in hydrochlorate form with chloro-ethoxyethanol. However, said procedures are carried out at high temperature (at xylene reflux (Teb=137-140° C.), and with mixtures of propanol and N-metthylpyrrolidone) over a long period of time, between 24 and 30 h, while also requiring a large excess of reagent in order to prevent undesired dialkylation reactions.

Later, international application WO 0155125 describes a procedure different from the preceding ones for obtaining the compound of formula (I). That procedure consists in reacting a derivative of haloethylpiperazineylthiazepine with ethylene glycol. This procedure requires both the use of sodium, an extremely strong deprotonisation agent, in order to generate the corresponding anion, and the use of a considerable excess of ethylene glycol (30 equivalents) in order to minimise the disubstitution reaction. The excess of ethylene glycol must be removed later with a large quantity of water, thereby generating a large quantity of residual aqueous products.

Furthermore, international application WO 9906381 describes a procedure for purifying the compound of formula (I), base quetiapine, by crystallisation and isolation as a solid. However, the implementation of this procedure has not permitted base quetiapine to be obtained in crystalline form.

DESCRIPTION OF THE INVENTION

Under a first aspect thereof, this invention discloses a new procedure for obtaining the 11-(4-[2-(2-hydroxyethoxy)ethyl]-1-piperazineyl)-dibenzo[b,f][1,4]thiazepine, of formula (I)

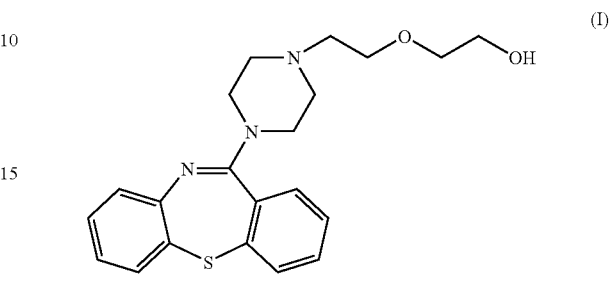

or a pharmaceutically acceptable salt thereof, which includes reaction between 2-(4-dibenzo[b,f][1,4]thiazepine-11-il-piperazine-1-il)ethanol, of formula (II), and a compound of formula (III):

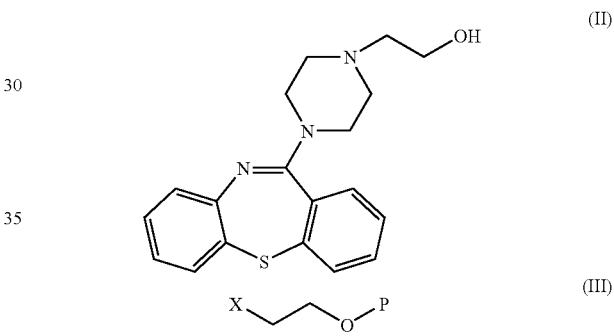

in which X means a leaving group and P a protective group of alcohols resistant to alkaline conditions, in the presence of a base, followed by a step of deprotection and, eventually, obtaining a pharmaceutically acceptable salt thereof.

In this invention "a protective group of alcohols resistant to alkaline conditions" is taken to mean a protective group of alcohols resistant to a pH>10 under aqueous conditions. See also "*Protective Groups in Organic Synthesis*, 3$^{rd}$ edition, T. W. Greene, Wiley Interscience, chapter 2" on protective groups of alcohols.

In this invention "in the presence of a base" is taken to mean in the presence of an alkaline or alkaline-earth organic or inorganic base, such as alkaline or alkaline-earth hydroxides or carbonates.

Advantageously, the use of the intermediate of formula (III) which has the hydroxyl group protected, prevents, without addition of an excess of reagent, the undesired disubstitution reactions taking place.

The leaving group X, (see M. B. Smith, J. March. March's Advanced Organic Chemistry, 5$^{th}$ Edition, New York (USA): John Wiley & Sons; 2001, pp 446), can be halogen or an alkylsulphonyloxy group, such as mesylate, triflate, nonaflate and tresylate, or an arylsulphonyloxy group, such as tosylate, brosylate, nosylate. Preferably, X is chloro or a p-toluenesulphonyloxy group (tosylate).

Preferably, the protective group P is of ether type, such as methyl-, ethyl- or benzylether, all of them optionally replaced.

Also preferably, the protective group P is a tetrahydropyranyl, benzyl or trityl (triphenylmethyl) group. More preferably still, P is a trityl group.

The reaction can be carried out within a wide range of temperatures between 0° C. and 130° C. Preferably, in a range of 25-70° C. when P is tertrahydropyranyl, 40 to 70° C. when P is benzyl and 80-120° C. when P is trityl.

Preferably, the procedure according to the invention is carried out by phase-transfer reaction between the compound of formula (II) and a compound of formula (III) in the presence of a phase-transfer catalyst. Advantageously a phase-transfer reaction permits the reaction to be carried out under softer temperature conditions, with shorter reaction times.

Advantageously, the phase-transfer reaction between the compound of formula (II) and the compound of formula (III) can be carried out in the absence of organic solvent, thereby avoiding the use of toxic solvents.

Preferably, the phase-transfer catalyst used is selected from among tetrabutyl ammonium bisulphate, Aliquat 336, tetrabutyl ammonium iodide, and ether 18-crown-6.

Preferably, the base is an alkaline hydroxide, such as sodium hydroxide or potassium hydroxide, in solid form or in aqueous solution.

The reaction takes place through the intermediate of formula (IV):

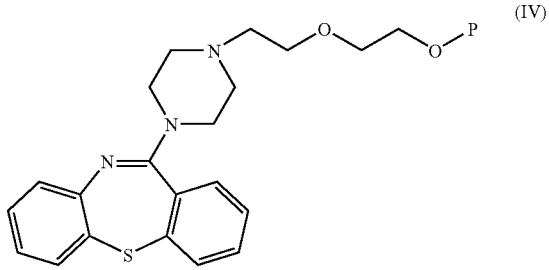

(IV)

in which P is as defined above.

If wished, the intermediate of formula (IV) can later be isolated by extraction with an organic solvent, preferably toluene.

The step of deprotection is then carried out, which can be by conventional methods. Preferably, the deprotection is carried out by hydrolysis of the intermediate (IV) in acid medium to yield the compound of formula (I).

Thus, when the protective group P is tetrahydropyranyl, the intermediate of formula (IV) is preferably not isolated, and the hydrolysis is carried out directly in the presence of an aqueous mineral acid.

When the protective group P is benzyl, the intermediate is preferably isolated, and the deprotection is carried out by means of acid hydrolysis, for example, with a solution of 33% hydrobromic acid in acetic acid.

And advantageously, when the protective group P is trithyl, the intermediate of formula (IV) obtained is a crystalline solid. This allows it to be purified by recrystallisation in organic solvents, such as methanol, ethylmethylketone or a mixture thereof. A high purity of this product is thereby obtained. Then, said recrystallised intermediate is later hydrolysed to the final compound of formula (I) in the presence of an acid such as acetic acid, trifluoroacetic acid, p-toluenesulphonic acid or hydrochloric acid, preferably p-toluenesulphonic acid, in an organic solvent such as toluene, methanol, isopropanol or a mixture thereof and, if wished, in the presence of water. The compound of formula (I) thus obtained is of very high purity, with no further purification of the compound being necessary.

Furthermore, when deprotection of the intermediate (IV) is carried out in the presence of acetic acid or anhydride, formation of the intermediate of formula (V) can occur.

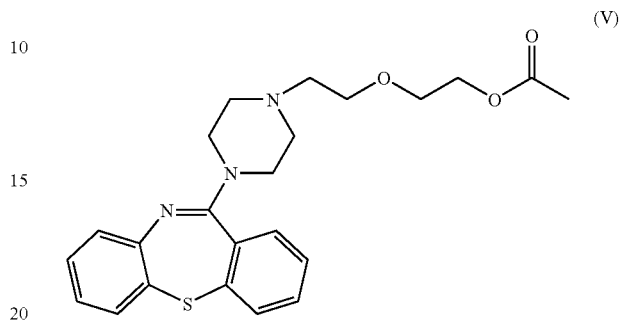

(V)

in which case specification is then carried out at ambient temperature to provide the end product of formula (I).

Finally, if wished, the compound of formula (I) is obtained in the form of a pharmaceutically acceptable salt. Preferably, the hemifumarate is obtained.

The intermediate of formula (II) can be obtained as described in patent CH 422793, by reaction of the aforesaid imino chloride with 2-piperazinyl-1-ethanol.

The intermediate of formula (III) can be obtained:

a) from the intermediate of formula (VI),

(VI)

by protecting the hydroxyl group with a protective group P of alcohols resistant to alkaline conditions, by means of conventional methods described in the literature, or b) from an intermediate of formula (VII)

(VII)

by insertion of the leaving group X by means of conventional methods, such as by halodehydroxylation reaction by treatment with hydracid acids of general formula HX or with halides of inorganic acids such as thionyl chloride or phosphorus pentachloride, or by treatment with an alkyl or arylsulphonyl chloride in the presence of a base.

In particular, the intermediate of formula III, in which P is tetrahydropyranyl (IIIa):

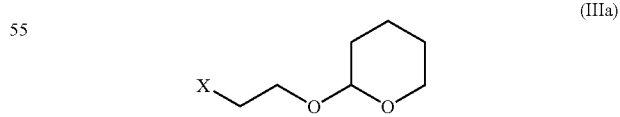

(IIIa)

and X is Cl or p-toluenesulphonyloxy, can be obtained easily by reaction of the 2-chloroethanol with 3,4-dihydro-2H-pyrane in the presence of various catalysts, as described in the literature (Synlett (1999), 8, 1261-1262), where X=Cl, and it can be obtained by reaction of 3,4-dihydro-2H-pyrane with excess of ethylene glycol in the presence of p-toluenesulphonic acid, followed by treatment with p-toluenesulphonyl chloride in the presence of triethylamine, as described in the literature (J. Org. Chem. (1993), 58(16), 4315-4325), when X=p-toluenesulphonyloxy.

In particular, the intermediate of formula III, in which P is benzyl (IIIb):

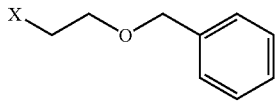

(IIIb)

and X is Cl, can be obtained by various procedures described in the literature, such as by treating the lithium salt of ethylene glycol benzyl bromide, followed by treatment with thionyl chloride, in the presence of pyridine (J. Org. Chem. (1979), 44 (7), 1163-1166).

In particular, the intermediate of formula III, in which P is trithyl (IIIc):

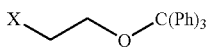

(IIIc)

and X is Cl can be obtained by reaction of triphenylchloromethane with 2-chloroethanol in the presence of pyridine, as described in the literature (Farmaco (1949), 4, 45-48).

Experimental Part

There follow, by way of non-restrictive explanation of the invention, the following examples.

EXAMPLES OF SYNTHESIS

Example 1

11-(4-[2-(2-hydroxyethoxy)ethyl]-1-piperazinyl) dibenzo[b,f][1,4]thiazepine (base Quetiapine)

To 26.2 mL of 50% aqueous solution of sodium hydroxide are added successively 5 g (14.7 mmols) de 2-(4-dibenzo[b,f][1,4]thiazepine-11-il-piperazine-1-il)ethanol, 10.43 g (63.4 mmols) of 2-(2-chloroethoxy)-tetrahydro-2H-pyrane and 0.49 g of tetrabutyl ammonium hydrogen sulphate. The mixture is heated at 60° C. for 6 hours with thorough stirring. It is cooled to 20-25° C., and 45 mL de toluene and 26 mL of water are added while agitating. The phases are separated and the organic phase is washed with water (2×26 mL). 32 mL of water and 5 mL of 35% hydrochloric acid 35% are added and the two-phase mixture is stirred at 20-25° C. for 3 hours. The phases are separated and the aqueous phase is washed successively with n-butanol (10 mL) and toluene (10 mL). Then 45 mL of toluene and 10% aqueous solution of potassium carbonate are added until the aqueous phase pH 10 is reached. The phases are separated and the aqueous phase is extracted with toluene (10 mL). The combined organic phases are evaporated to dryness under vacuum, yielding 4.80 g (85%) of the product of the title as a light yellow oil.

IR (film), cm$^{-1}$: 3045, 2920, 2855, 1600, 1570, 1550, 1455, 1410, 1305, 1250, 1240, 1140, 1115, 1016, 755.

$^1$H-RMN (CDCl$_3$), δ (ppm): 2.5-2.8 (m, 6H, —CH$_2$—N (CH$_2$—)—CH$_2$—), 3.4-3.8 (m, 11H, —CH$_2$—N(C=)—CH$_2$—+—CH$_2$—O—CH$_2$—CH$_2$—OH), 6.8-7.6 (m, 8H, Ar).

Example 2

11-(4-[2-(2-hydroxyethoxy)ethyl]-1-piperazinyl) dibenzo[b,f][1,4]thiazepine (base Quetiapine)

To 10.43 g (63.4 mmols) of 2-(2-chloroethoxy)-tetrahydro-2H-pyrane are added successively 5 g (14.7 mmols) of 2-(4-dibenzo[b,f][1.4]thiazepine-11-il-piperazine-1-il)ethanol, 5 g of powdered potassium hydroxide and 0.49 g 18-corona-6 catalyst. The mixture is heated at 40° C. for 6 hours with thorough stirring. The synthesis proceeds as in Example 1, yielding 4.65 g (82%) of the product of the title as a light yellow oil, having IR and $^1$H-RMN spectra identical to those of the product obtained in Example 1.

Example 3

11-(4-[2-(2-hydroxyethoxy)ethyl]-1-piperazinyl) dibenzo[b,f][1,4]thiazepine (base Quetiapine)

To 10.43 g (63.4 mmols) of 2-(2-chloroethoxy)-tetrahydro-2H-pyrane are added successively 5 g (14.7 mmols) of 2-(4-dibenzo[b,f][1.4]thiazepine-11-il-piperazine-1-il)ethanol, 5 g of powdered potassium hydroxide and 0.49 g of Aliquat 336 catalyst. The mixture is heated at 40° C. for 20 hours with thorough stirring. The synthesis proceeds as in Example 1, yielding 4.23 g (75%) of the product of the title as a light yellow oil, having IR and $^1$H-RMN spectra identical to those of the product obtained in Example 1.

Example 4

11-(4-[2-(2-hydroxyethoxy)ethyl]-1-piperazinyl) dibenzo[b,f][1,4]thiazepine (base Quetiapine)

To 26.2 mL of 50% aqueous solution of sodium hydroxide are added successively 5 g (14.7 mmols) of 2-(4-dibenzo[b,f][1.4]thiazepine11-il-piperazine-1-il)ethanol, 19 g (63.3 mmols) of p-toluenesulphonate of 2-(tetrahydropyrane-2-yloxy)ethyl and 0.5 g of tetrabutyl ammonium hydrogen sulphate. The mixture is heated at 60-65° C. for 8 hours with thorough stirring. The synthesis proceeds as in Example 1, yielding 5.08 g (90%) of the product of the title as a light yellow oil, having IR and $^1$H-RMN spectra identical to those of the product obtained in Example 1.

Example 5

11-(4-[2-(2-hydroxyethoxy)ethyl]-1-piperazinyl) dibenzo[b,f][1,4]thiazepine (base Quetiapine)

11-{4-[2-(2-benzylxiethoxy)ethyl]piperazine-1-il}-dibenzo[b,f][1,4]thiazepine

To 26.2 mL of 50% aqueous solution of sodium hydroxide are added successively 5 g (14.7 mmols) of 2-(4-dibenzo[b,f][1.4]thiazepine-11-il-piperazine-1-il)ethanol, 10.81 g (63.3 mmols) of benzyl-(2-chloroethyl)-ether and 0.49 g of tetrabutyl ammonium hydrogen sulphate. The mixture is heated at 60° C. for 9 hours with thorough stirring. It is cooled to 20-25° C. and 45 mL of toluene and 26 mL of water are added while stirring. The phases are separated and the organic phase is washed with water (2×26 mL). 75 mL of water and 5 mL of 35% hydrochloric acid are added to the toluene phase and the two-phase mixture is stirred at 20-25° C. for 5 min. The phases are separated and the toluene phase is washed with 10 mL of water. 90 mL of toluene and 10 mL of 25% ammonium hydroxide are added to the combined aqueous phases while stirring. The phases are separated and the organic phase is evaporated to dryness under vacuum, yielding 6.49 g (93%) of 11-{4-[2-(2-benzyl-oxy-ethoxy)ethyl]piperazine-yl}-dibenzo[b,f][1.4]thiazepine as a yellow oil.

IR (film), cm$^{-1}$: 3040, 2850, 1585, 1550, 1430, 1290, 1090, 1000, 725.

$^1$H-RMN (CDCl$_3$), δ (ppm): 2.4-2.8 (m, 6H, —CH$_2$—N(CH$_2$—)—CH$_2$—), 3.4-3.8 (m, 10H, —CH$_2$—N(C=)—CH$_2$—+—CH$_2$—O—CH$_2$—CH$_2$—O—), 4.6 (s, 2H, —O—CH$_2$—C$_6$H$_5$), 6.8-7.6 (m, 13H, Ar).

2-[2-(4-dibenzo[b,f][1,4]thiazepine-11-il-piperazine-1-il)ethoxy]ethylo acetate 1 g (2.11 mmol) of 11-{4-[2-(2-benzylxiethoxy)ethyl]piperazine-1-il}-dibenzo[b,f]-[1,4]thiazepine are added to a mixture made up of 5 mL of 33% HBr in acetic acid and 5 mL of acetic acid. The mixture is kept at 20-25° C. with stirring for 1.5 h. It is concentrated to dryness under vacuum. The residue obtained is treated with 25 mL of water and 25 mL of dichloromethane, is neutralised with solid NaHCO$_3$ and the phases separated. The aqueous phase is extracted with dichloromethane (25 mL) and the combined organic phases are dried with anhydrous sodium sulphate and evaporated to dryness under vacuum, yielding 0.8 g (89%) of 2-[2-(4-dibenzo[b,f][1.4]thiazepine-11-il-piperazine-1-il)ethoxy]ethylo acetate as a yellow oil.

IR (film), cm$^{-1}$: 3045, 2940, 2860, 1725, 1600, 1560, 1440, 1290, 1235, 1110, 1035, 1000, 750, 730.

$^1$H-RMN (CDCl$_3$), δ (ppm): 2.05 (s, 3H, —COCH$_3$), 2.5-2.8 (m, 6H, —CH$_2$—N(CH$_2$—)—CH$_2$—), 3.4-3.8 (m, 8H, —CH$_2$—N(C=)—CH$_2$—+—CH$_2$—O—CH$_2$—), 4.2 (t, 2H, —CH$_2$—OAc), 6.8-7.6 (m, 8H, Ar).

11-(4-[2-(2-hydroxyethoxy)ethyl]-1-piperazinyl)dibenzo[b,f][1,4]thiazepine (base Quetiapine)

0.27 g (4.09 mmol) of powdered potassium hydroxide are added to a solution of 0.65 g (1.53 mmol) pf 2-[2-(4-dibenzo[b,f][1.4]thiazepine-11-il-piperazine-1-il)ethoxy]ethylo acetate in 7 mL of methanol. The mixture if kept at 20-25° C. with stirring for 3 h and is concentrated to dryness under vacuum. The residue is treated with 25 mL of HCl 1 N. The resulting solution is washed with 5 mL of n-Butanol and 25 mL of toluene. The aqueous phase is basified to pH 10 with aqueous solution of 20% sodium hydroxide and is extracted successively with 25 and 10 mL of toluene. The combined organic phases are evaporated to dryness under vacuum to yield 0.55 g (94%) of the product of the title as a light yellow oil, having IR and $^1$H-RMN spectra identical to those of the product obtained in Example 1.

Example 6

11-(4-[2-(2-hydroxyethoxy)ethyl]-1-piperazinyl)dibenzo[b,f][1.4]thiazepine (base Quetiapine)

11-{4-[2-(2-tritiloxiethoxy)ethyl]piperazine-1-il}dibenzo[b,f][1,4]thiazepine

A mixture of 40 g (0.12 mols) of 2-(4-dibenzo[b,f][1,4]thiazepine-11-il-piperazine-1-il)ethanol and 44 g (0.14 mols) of trityl-(2-chloroethyl)-ether are heated slowly to 100-110° C. until the mixture has fused completely. Stirring is started, and 4 fractions of 5 g of powdered potassium hydroxide are added over the course of 45-60 min, while keeping the temperature at 110-115° C. 1.6 g of 18-corona-6 catalyst are added and the mixture kept under stirring at 110-115° C. for 2 hours. 300 mL of toluene are added slowly until the reaction mixture has dissolved, and then 100 mL of water are added. It is left to cool to 20-25° C. and the phases are separated. The organic phase is washed with a solution of 5 g of sodium chloride in 50 mL of water and the organic phase is evaporated to dryness under vacuum. The residue is dissolved by adding 80 mL of toluene and 160 mL of methanol at 40° C. The mixture is kept under stirring at 35-40° C. and the product precipitated by slow addition of 250 mL of methanol. The suspension is cooled to 0-5° C. and the solid is filtered, and then dried at 45° C., yielding a crude product of 64 g of 11-{4-[2-(2-trityloxyethoxy)ethyl]piperazine-1-il}dibenzo-[b,f][1,4]thiazepine with a richness of 90-92%.

The above crude product is purified by recrystallisation of a mixture at reflux of 125 mL of ethylmethylketone and 200 mL of methanol. It is cooled slowly to 20-25° C. and the mixture is kept under stirring at this temperature for 1 hour. It is then cooled to 0-5° C. The solid obtained is filtered, washed with 50 mL of a cold mixture of methanol/ethylmethylketone (5:1) and finally with 60 mL of cold methanol. The product is dried at 45° C., yielding 60.8 g (82%) of 11-{4-[2-(2-trityloxyethoxy)ethyl]piperazine-1-il}dibenzo[b,f][1.4]-thiazepine as a light yellow solid of high purity (>99.5%).

m.p.: 119-121° C.

IR (KBr), cm$^{-1}$: 3055, 2940, 2800, 1575, 1560, 1450, 1385, 1245, 1015, 765, 705.

$^1$H-RMN (CDCl$_3$), δ (ppm): 2.4-2.8 (m, 6H, —CH$_2$—N(CH$_2$—)—CH$_2$—), 3.2 (t, 2H, —CH$_2$—O-Tr), 3.4-3.8 (m, 8H, —CH$_2$—N(C=)—CH$_2$—+—CH$_2$—O—CH$_2$—), 6.8-7.6 (m, 23H, Ar).

11-(4-[2-(2-hydroxyethoxy)ethyl]-1-piperazinyl)dibenzo[b,f][1,4]thiazepine (base Quetiapine)

A mixture of 1 kg (1.6 mols) of 11-{4-[2-(2-trityloxyethoxy)ethyl]piperazine-1-il}dibenzo[b,f][1.4]-thiazepine, 3.5 L of toluene, 1.5 L of methanol and 0.468 kg of p-toluenesulphonic monohydrate acid is kept at reflux for 4 hours. The solvent is evaporated to dryness under vacuum and the residue is dissolved by adding 5 L of water, 2 L of toluene and 0.2 L of 35% hydrochloric acid while stirring. The phases are separated. The organic phase is extracted with 0.6 L of water. To the combined aqueous phases are added 2.7 L of toluene and 50% aqueous solution of sodium hydroxide to pH 9,5. The phases are decanted and the aqueous phase is extracted with 0.6 L of toluene. The combined organic phases are filtered through diatomaceous earth and evaporated to dryness under vacuum, yielding 0.580 kg (95%) of the product of the title as a light yellow oil, having IR and $^1$H-RMN spectra identical to those of the product obtained in Example 1.

11-(4-[2-(2-hydroxyethoxy)ethyl]-1-piperazinyl)dibenzo[b,f][1.4]thiazepine hemifumarate 94.4 g (0.81 mols) of fumaric acid at 20-25° C. are added to a stirred solution of the above residue of 0.580 (1.52 mols) of 11-(4-[2-(2-hydroxyethoxy)ethyl]-1-piperazinyl)dibenzo[b,f][1.4]thiazepine in 3.06 L of methanol. A solid is precipitated after 5-15 min. Stirring is maintained at 20-25° C. for 30 min. The suspension is heated again at reflux for 5 min. and then cooled to 10-15° C. The suspension is stirred at this temperature for 1 hour. The solid is filtered and washed with cold methanol (2×0.5 L) and then dried under vacuum at 45° C., yielding 0.63 kg (94%) of the product of the title of high purity (>99.7%).

m.p.: 172-174° C.

IR (KBr), cm$^{-1}$: 3320, 3075, 2945, 2870, 1575, 1415, 1335, 1130, 1085, 990, 795, 770.

$^1$H-RMN (CD$_3$OD), δ (ppm): 3.1-3.5 (m, 6H, —CH$_2$—N (CH$_2$—)—CH$_2$—), 3.5-3.9 (m, 10H, —CH$_2$—N(C=)—CH$_2$—+—CH$_2$—O—CH$_2$—CH$_2$—OH), 6.6 (s, 1H, ½fumarate), 6.9-7.6 (m, 8H, Ar).

The invention is:

1. Procedure for obtaining 11-(4-[2-(2-hydroxyethoxy)ethyl]-1-piperazinyl)-dibenzo[b,f] [1,4]thiazepine, of formula (I)

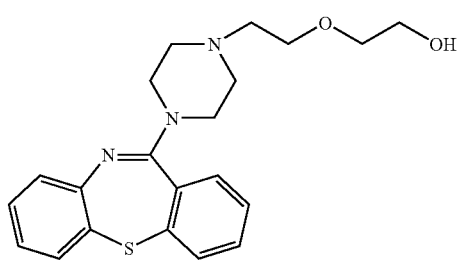

or a pharmaceutically acceptable salt thereof, wherein it comprises reaction between compound of formula (II) and a compound of formula (III):

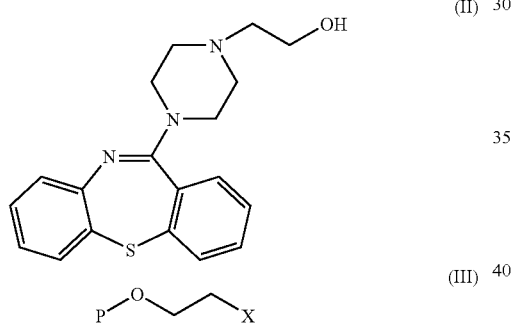

in which X means a leaving group and P a protective group of alcohols resistant to alkaline conditions, in the presence of a base, followed by a step of deprotection and, eventually, obtaining a pharmaceutically acceptable salt thereof.

2. Procedure according to claim 1, wherein said reaction between said compound of formula (II) and said compound of formula (III) is carried out by phase transfer in the presence of a phase-transfer catalyst.

3. Procedure according to claim 2, wherein said phase-tranfer catalyst is selected from among tetrabutyl ammonium bisulphate, Aliquat 336, tetrabutyl ammonium iodide, 18-crown-6-ether.

4. Procedure according to claim 2, wherein said phase-transfer reaction is carried out in the absence of organic solvent.

5. Procedure according claim 1, wherein said base is an alkaline or alkaline-earth organic or inorganic base.

6. Procedure according to claim 1, wherein said base is an alkaline or alkaline-earth hydroxide or carbonate.

7. Procedure according to claim 6, wherein said base is an alkaline hydroxide in solid form or in aqueous solution.

8. Procedure according to claim 1, wherein X is halogen or an alkylsulphonyloxy or arylsulphonyloxy group.

9. Procedure according to claim 8, wherein X is a mesylate, triflate, nonaflate, 2,2,2-trifluoro-ethane-sulfonate, tosylate, brosylate or nosylate.

10. Procedure according to claim 1, wherein said protective group of alcohols P is of ether type.

11. Procedure according to claim 10, wherein said protective group of alcohols P of ether type is selected from tetrahydropyranyl, benzyl and trityl (triphenylmethyl).

12. Procedure according to claim 11, wherein said protective group of alcohols P of ether type is trityl.

13. Procedure according to claim 1, wherein said step of deprotection includes hydrolysis in acid medium of an intermediate of formula (IV):

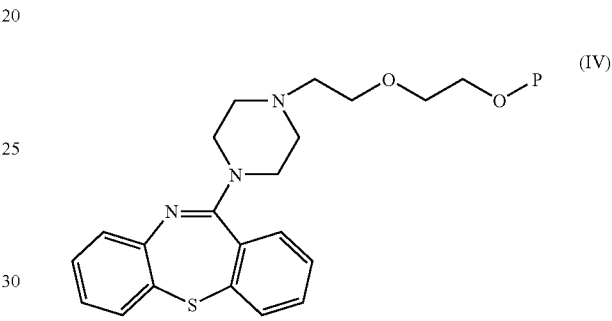

in which P has the meaning defined in claim 1.

14. Intermediate of formula (IV):

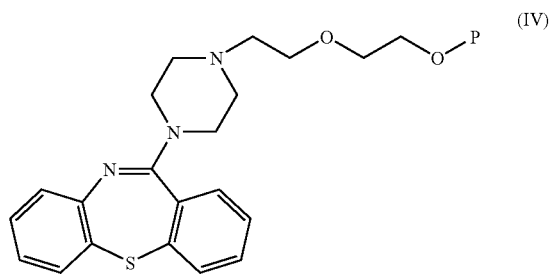

in which P is a protective group of alcohols resistant to alkaline conditions.

15. Intermediate of formula (IV) according to claim 14, wherein said protective group of alcohols P is of ether type.

16. Intermediate of formula (IV) according to claim 15, wherein said protective group of alcohols P is of ether type is selected from tetrahydropyranyl, benzyl and trityl (triphenylmethyl).

17. Intermediate of formula (IV) according to claim 15, wherein said protective group of alcohols P of ether type is trityl.

* * * * *